United States Patent
Lin

(10) Patent No.: US 6,745,775 B2
(45) Date of Patent: Jun. 8, 2004

(54) METHODS AND APPARATUS FOR PRESBYOPIA TREATMENT USING A SCANNING LASER SYSTEM

(75) Inventor: J. T. Lin, Oviedo, FL (US)

(73) Assignee: Surgilight, Inc., Orlando, FL (US)

( * ) Notice: Subject to any disclaimer, the term of this patent is extended or adjusted under 35 U.S.C. 154(b) by 20 days.

(21) Appl. No.: 09/794,496

(22) Filed: Feb. 28, 2001

(65) Prior Publication Data

US 2001/0016736 A1 Aug. 23, 2001

Related U.S. Application Data

(63) Continuation-in-part of application No. 09/189,609, filed on Nov. 10, 1998, now Pat. No. 6,263,879.

(51) Int. Cl.$^7$ ............................................... A61B 19/00
(52) U.S. Cl. ........................................ 128/898; 606/5
(58) Field of Search ............................. 606/5; 128/898

(56) References Cited

U.S. PATENT DOCUMENTS

| 4,907,586 A | 3/1990 | Bille et al. ............... 606/5 |
| 5,144,630 A | 9/1992 | Lin ............................ 606/5 |
| 5,354,331 A | 10/1994 | Schachar .................. 623/4 |
| 5,484,432 A | 1/1996 | Sand ......................... 606/5 |
| 5,489,299 A | 2/1996 | Schachar .................. 623/4 |
| 5,520,679 A | 5/1996 | Lin ............................ 606/5 |
| 5,529,076 A | 6/1996 | Schachar .................. 606/4 |
| 5,533,997 A | 7/1996 | Ruiz .......................... 606/5 |
| 5,722,952 A | 3/1998 | Schachar .................. 606/4 |
| 6,258,082 B1 * | 7/2001 | Lin ............................ 372/37 |

OTHER PUBLICATIONS

Spencer Thornton, Chapt. 4, "Surgery for Hyperopia and Presbyopia" edited by Neal Sher (Williams & Wilkins, MD, 1997).

* cited by examiner

Primary Examiner—Corrine McDermott
Assistant Examiner—Thomas C Barrett
(74) Attorney, Agent, or Firm—Knobbe, Martens, Olson & Bear, LLP.

(57) ABSTRACT

Presbyopia is treated by a method which uses various lasers to remove a portion of the scleral tissue and increase the accommodation of the presbyopic patient's eye. Stable accommodation is achieved by the filling of the sub-conjunctival tissue to the laser-ablated scleral areas. The proposed laser wavelength ranges from ultraviolet to infrared of (0.15–0.36) microns, (0.5–1.4) microns and (0.9–10.6) microns. Both scanning and fiber delivered systems are proposed.

30 Claims, 3 Drawing Sheets

METHODS AND APPARATUS FOR PRESBYOPIA TREATMENT USING A SCANNING LASER SYSTEM

This is a Continuation-in-part of application Ser. No. 09/189,609 filed on Nov. 10, 1998 now U.S. Pat. No. 6,263,879.

BACKGROUND OF THE INVENTION

1. Field of the Invention

The present invention relates to apparatus and methods for the treatment of presbyopia using scanning and fiber-coupled lasers to ablate the sclera tissue.

2. Prior Art

Corneal reshaping, including a procedure called photorefractive keratectomy (PRK) and a new procedure called laser assisted in situ keratomileusis, or laser intrastroma keratomileusis (LASIK), has been performed by lasers in the ultraviolet (UV) wavelength of 193–213 nm. Commercial UV refractive lasers include ArF excimer lasers at 193 nm and other non-excimer, solid-state lasers, such as the one patented by the present inventor in 1992 (U.S. Pat. No. 5,144,630). Precise, stable corneal reshaping requires lasers with strong tissue absorption (or minimum penetration depth) such that the thermal damage zone is at a minimum (less than few microns). Furthermore, accuracy of the procedure of vision correction depends on the amount of tissue removed in each laser pulse, in the order of about 0.2 microns. Therefore, lasers at UV wavelengths between 193 and 213 nm and at the mid-infrared wavelengths between 2.8 and 3.2 microns are two attractive wavelength ranges which match the absorption peak of protein and water, respectively.

The above-described prior arts are however limited to the use of reshaping the corneal surface curvature for the correction of myopia and hyperopia. A variation of farsightedness that the existing laser surgery procedures will not treat is presbyopia, the gradual age related condition of suddenly fuzzy print and the necessity of reading glasses. When a person reaches a certain age (around 45), the eyes start to lose their capability to focus sharply for near vision. Presbyopia is not due to the cornea but comes about as the lens loses its ability to accommodate or focus sharply for near vision as a result of loss of elasticity that is inevitable as people age.

The present patent uses a "cold" laser to remove sclera tissue (outside the limbus area) versus a "thermal" lasers in Sand's patent (U.S. Pat. No. 5,484,432) to shrink the corneal shape (inside the limbus area). The cold laser of the present has a wavelength range of (0.15–0.36) microns and (2.6–3.2) microns which are also different from that of the "thermal" laser range of (1.80–2.55) microns proposed by Sand.

The prior arts of Ruitz (U.S. Pat. No. 5,533,997) and Lin (U.S. Pat. No. 5,520,679) are all limited to the corneal central portion and are designed to change the curvature of the cornea by ablation the surface layer of the cornea. The present patent, on the contrary, does not change the corneal central curvature and only ablating tissue outside the limbus.

The technique used in the prior art of Bille (U.S. Pat. No. 4,907,586) is specified to below conditions: (a) quasi-continuous laser having pulse duration less than 10 picoseconds and focused spot less than 10 micron diameter; (b) the laser is confined to the interior of a selected tissue to correct myopia, hyperopia or astigmatism, and (c) the laser is focused into the lens of an eye to prevent presbyopia. He also proposed to use laser to create a cavity within the corneal stroma to change its visco-elastic properties.

The "presbyopia" correction proposed by Ruitz using an excimer (ArF) laser also required the corneal surface to be reshaped to form "multifocal" effort for a presbyopia patents to see near and far. However, Ruitz's "presbyopia" correction is fundamentally different from that of the present patent which does not change the corneal curvature and only ablate the scleral tissue outside the limbus area. In the present patent, we propose that the presbyopia patent is corrected by increasing patient's accommodation rather than reshaping the cornea into "multifocal".

To treat presbyopic patients, or the reversal of presbyopia, using the concept of expanding the sclera by mechanical devices has been proposed by Schachar in U.S. Pat. Nos. 5,489,299, 5,722,952, 5,465,737 and 5,354,331. These mechanical approaches have the drawbacks of complexity and are time consuming, costly and have potential side effects. To treat presbyopia, the Schachar U.S. Pat. Nos. 5,529,076 and 5,722,952 propose the use of heat or radiation on the corneal epithelium to arrest the growth of the crystalline lens and also propose the use of lasers to ablate portions of the thickness of the sclera. However, these prior arts do not present any details or practical methods or laser parameters for the presbyopic corrections. No clinical studies have been practiced to show the effectiveness of the proposed concepts. The concepts proposed in the Schachar patents regarding lasers suitable for ablating the sclera tissues were incorrect because he did not identify which lasers are "cold lasers". Many of his proposed lasers are thermal lasers which will cause thermal burning of the cornea, rather than tissue ablation. Furthermore, the clinical issues, such as locations, patterns and depth of the sciera tissue removal were not indicated in these prior patents. In addition, it is essential to use a scanning laser to achieve the desired ablation pattern and to control the ablation depth on the sclera tissue. Schachar's methods also require the weakening of the sclera and increase its diameter by expansion.

Another prior art proposed by Spencer Thornton (Chapter4, "Surgey for hyperopia and presbyopia", edot3d by Neal Sher (Williams & Wilkins, MD, 1997) is to use a diamond knife to incise radial cuts around the limbus areas. It requires a deep (90%–98%) cut of the sclera tissue in order to obtain accommodation of the lens. This method, however, involves a lot of bleeding and is difficult to control the depth of the cut which requires extensive surgeon's skill.

Another drawback for presbyopia correction provided by the above-described non-laser methods is the major post-operative regression of about (30%–80%). And this regression is minimum in the laser method proposed in the present invention. The important concept proposed in the present invention is to support the post-operative results which show minimum regression. We proposed that the laser ablated sclera tissue "gap" will be filled in by the sub-conjunctival tissue within few days after the surgery. This filled in sub-conjunctival tissue is much more flexible than the original sclera tissue. Therefore the filled-in gap in the sclera area will cause the underlaying ciliary body to have more space to move. This in turn will allow the ciliary body to contract or expand the zonular fiber which is connected to the lens, when the presbyopic patient is adjusting his lens curvature to see near and far. The above described sub-conjunctival tissue filling effects and the increase of "flexibility" of the sclera area are fundamentally different from the scleral "expansion" (or weakening) concept proposed by the prior arts of Schachar and proposed by the implant of a scleral band. In the present invention, the laser ablated sclera area is not weakening, it becomes more flexible instead.

One objective of the present invention is to provide an apparatus and method to obviate these drawbacks in the above Schachar patents.

It is yet another objective of the present invention to use a scanning device such that the degree of ciliary mussel accommodation can be controlled by the location, size and shapes of the removed sclera tissue.

It is yet another objective of the present invention to define the non-thermal lasers for efficient tissue ablation.

It is yet another objective of the present invention to define the optimal laser parameters and the ablation patterns for best clinical outcome for presbyopia patients, where sclera ablation will increase the accommodation of the ciliary mussel by the increase of the flexibility in the laser-ablated areas.

It is yet another objective of the present invention to provide the appropriate scanning patterns which will cause effective ciliary body contraction and expansion on the zonules and the lens.

It is yet another objective of the present invention to provide a new mechanism which supports the clinical results of laser presbyopia correction with minimum regression. One important concept proposed in the present invention is to support the post-operative results which show minimum regression when presbyopia is corrected by a laser ablation for the sclera tissue.

We proposed that the laser ablated sclera tissue "gap" will be filled in by the sub-conjunctival tissue within few days after the surgery. This filled in sub-conjunctival tissue is much more flexible than the original sclera tissue. Therefore the filled-in gap in the sclera area will cause the underlaying ciliary body becomes more flexible. This will allow the ciliary body to contract or expand the zonular fiber connected to the lens when the presbyopic patient is adjusting his lens curvature to see near and far.

The concept presented in the present patent is to remove, by any methods including laser or non-laser methods, portion of the sclera tissue which is filled in by sub-conjunctival tissue to increase the flexibility of the scleral area and in turn causes the movement of the ciliary body and zonular fiber to increase the lens accommodation.

SUMMARY OF THE INVENTION

The preferred embodiments of the present surgical laser consists of a combination of an ablative-type laser and delivery unit. The ablative-type laser has a wavelength range of from 0.15 to 0.35 microns and from 2.6 to 3.2 microns and is operated in a pulsed mode such that the thermal damage of the corneal tissue is minimized.

It is yet another preferred embodiment of the present surgical laser to provide a scanning mechanism to effectively ablate the sclera tissue at a controlled depth by beam overlapping or by controlling the number of laser pulses acting on the sclera.

It is yet another embodiment of the present surgical laser to provide an integration system in which the ablative laser may be delivered by a scanner or by a fiber-coupled device which can be manually scanned over the cornea.

It is yet another embodiment of the present surgical laser to focus the laser beams to generate the sclera ablation patterns in radial lines, curved lines, dotted rings, or a slit pattern.

It is yet another embodiment of the present surgical laser to provide an integration system in which the sclera ablation leads to the increase of the accommodation of the ciliary muscle for the treatment of presbyopia and the prevention of open angle glaucoma.

It is yet another preferred embodiment of the present application to provide a non-laser mechanical method including a diamond knife to remove a portion of the scleral tissue and cause the movement of the ciliary body for lens accommodation.

Further preferred embodiments of the present surgical laser will become apparent from the description of the invention which follows.

DETAILED DESCRIPTION OF THE INVENTION AND THE PREFERRED EMBODIMENTS

Figure 1:
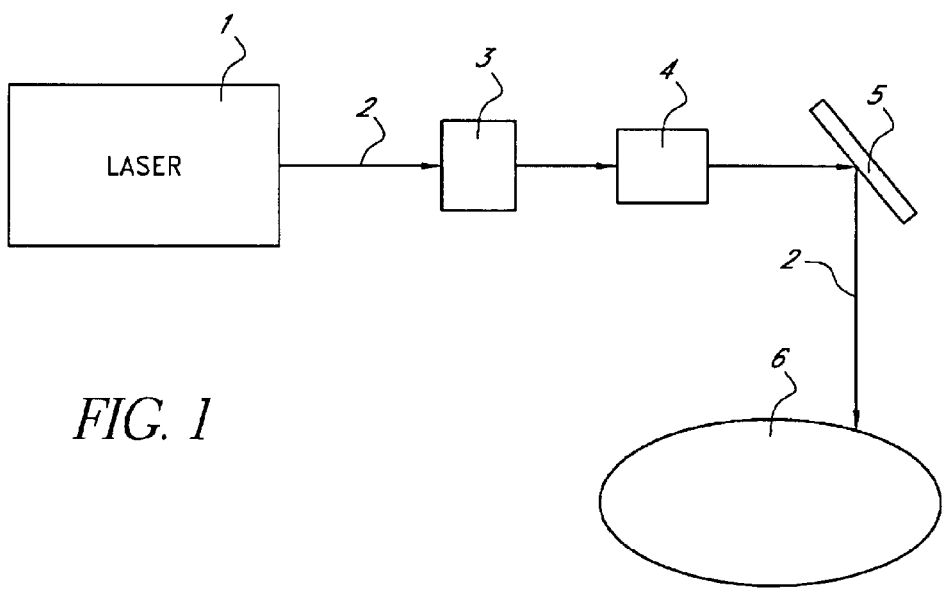
FIG. 1 is a block diagram of an integrated laser system consisting of an ablative laser coupled to the cornea by a reflection mirror and a scanning device.

FIG. 1 of the drawings is a schematic of a laser system having an ablative laser 1 producing a laser beam 2 of a predetermined wavelength and focused by a lens 3 which is directed onto a scanner 4 and then reflected by a mirror 5 onto the cornea 6 of a patient's eye. The scanner 4 consists of a pair of motorized coated mirrors with a 45 degree highly reflecting both the ablative laser beam 2. The mirrors 4 is highly reflective to the wavelength of the beams 2. The focusing lens 3 has a focal length of about 10–100 cm such that the spot size of the ablative laser beam 2 is about 0.1–1.0 mm on the corneal surface. In FIG. 1, the ablative laser beams 2 is scanned by the scanner 4 over the corneal sclera area of the eye 6 to generate predetermined patterns. An alternative embodiment of the present surgical laser is to use a cylinder lens to focus the ablative laser 1 to a line spot with a size of 0.1-0.8 mm×3.0–5.0 mm on the corneal surface to eliminate the need of scanner 4. Furthermore, the scanner may consist a motorized mirrors or a refractive optical device such that the ablative laser is delivered to the cornea surface in predetermined patterns.

The preferred embodiment of the laser 1 includes an ablative laser such as a Er:YAG laser; Er:YSGG laser; an optical parametric oscillation (OPO) laser at (2.6–3.2) microns; a gas laser with a wavelength of (2.6–3.2) microns; an excimer laser of ArF at 193 nm; a XeCl excimer laser at 308 nm; a frequency-shifted solid state laser at (0.15–3.2) microns; the harmonic generation of Nd:YAG or Nd:YAL or Ti:sapphire laser at wavelenegth of about (190–220) nm; a CO laser at about 6.0 microns and a carbon dioxide laser at 10.6 microns; a diode laser at (0.8–2.1) microns, or any other gas or solid state lasers including flash-lamp and diode-laser pumped, at (0.5–10.6) microns spectra range. To achieve the ablation of the sclera tissue at the preferred laser spot size of (0.1–1.0) mm requires an ablative laser energy per pulse of about (0.1–20) mJ depending on the pulse duration and the laser beam spot size.

For a typical pulse laser width of 100 nanoseconds to 500 microseconds, the preferred embodiments of FIG. 1 shall require the ablative laser to meet the peaks of tissue absorption spectra such as 0.98, 1.5, 2.1, 2.94 and 6.0 microns. However, for the case of lasers with a very short pulse of about from 1 femtosecond to 1 nanoseconds, the laser wavelength becomes non-critical in the tissue interaction and the high peak laser intensity with small laser spot are more important. Therefore, The preferred embodiment of the laser 1 should also include the short pulse lasers having wavelength of about (0.5–1.4) microns, such as Nd:YAG or Nd:YLF laser and their second harmonics operated in the range of picosecond or femtosecond pulse width.

Figure 2:
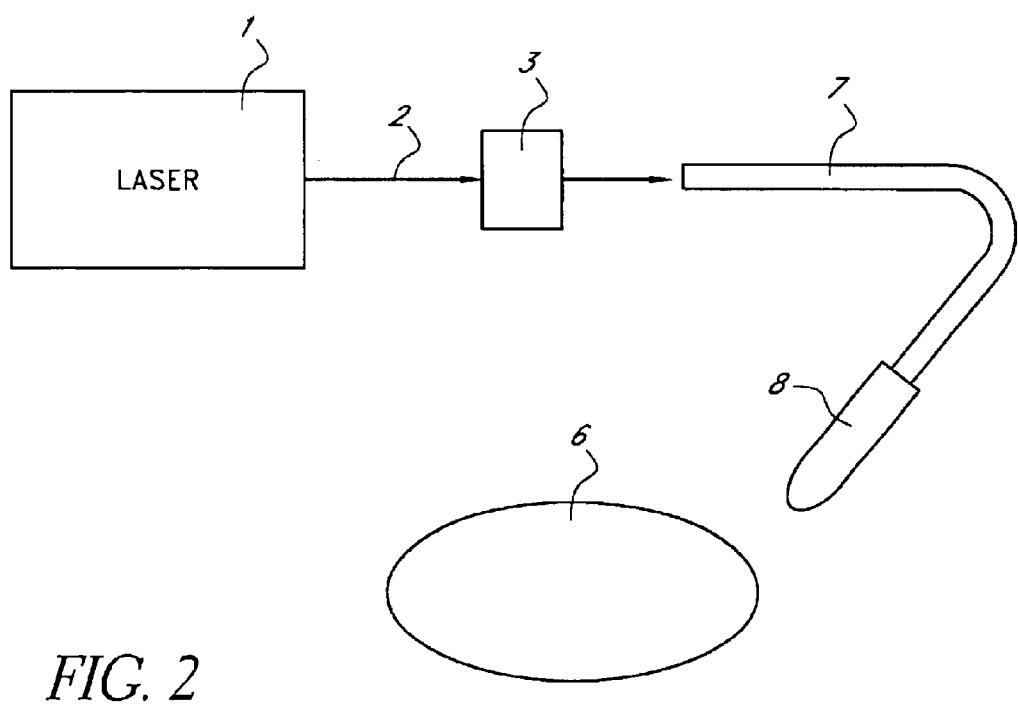
FIG. 2 is a block diagram of a laser system where the ablative laser is fiber-coupled and manually delivered to the cornea.
Figure 3:
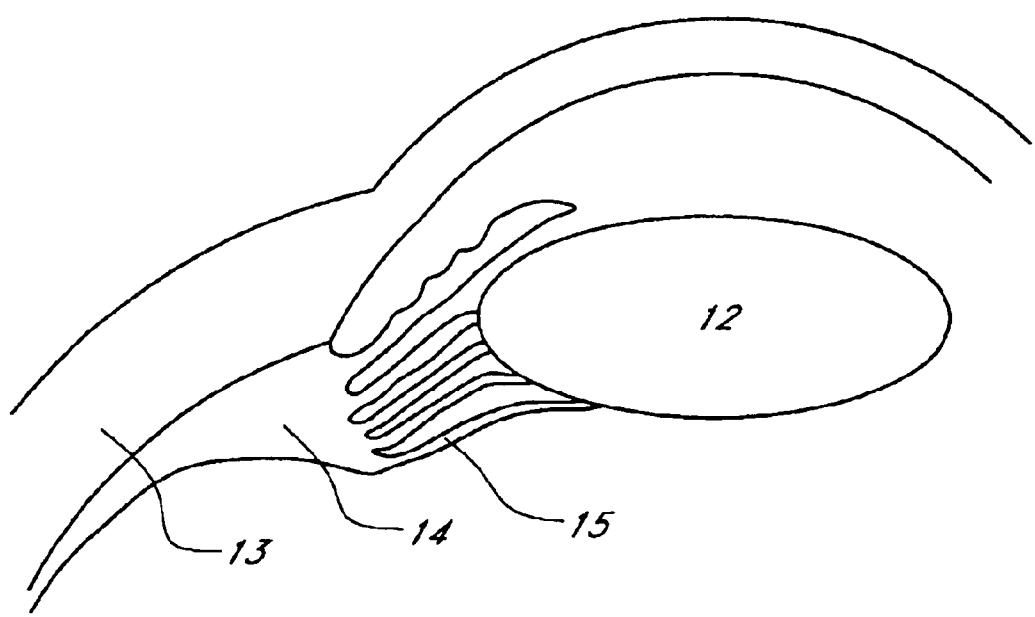
FIG. 3 is the schematic drawing of the anterposterior section through the anterior portion of a human eye showing the sclera, ciliary muscle, zonule and the lens.

Referring to FIG. 2, the ablative laser 1 has the same schematic as that of FIG. 1 where the laser beam 2 is coupled to an optical fiber 7 and delivered to the cornea 6 by a hand piece 8. Another embodiment may use an optical fiber or an articulate arm to deliver the ablative laser beams such that the presbyopia treatment may be conducted manually without the need of a scanner or reflecting mirrors. For the fiber delivered system, a fiber tip connected to the fiber hand piece is preferred such that sterilization may be done only on the fiber tip. FIG. 3 shows the lens of a human eye 12 connected to the sclera tissue 13 and the ciliary body 14 by zonule fibers 15. When portion of the sclera tissue 13 is removed by an ablative laser, this "gap" will be filled in by the sub-conjunctival tissue which is much more flexible than the original sclera tissue. This filled in sub-conjunctiva will allow the ciliary body 14 to contract or expand the zonular fiber 15 which is connected to the lens, when the presbyopic patient is adjusting his lens curvature to see near and far. Ablation of the sclera 13 will cause the ciliary muscle to contract and the lens becomes more spherical in topography with a shorter radii of curvature for near objects. The reversed process of ciliary muscle relaxation will cause a longer radii of curvature for distant objects. Therefore, laser ablation of the sclera tissue will increase the accommodation of the ciliary body for the presbyopic patient to see both near and distance.

For efficient accommodation, the depth of the laser ablation needs to be approximately (60%–90%) of the sclera thickness which is about (500–700) microns. For safety reasons, the ablation depth should not cut through the choroid. It is therefore clinically important that the patient's sclera thickness be measured pre-operatively and the laser ablation depth controlled. A scanning laser is used to control this depth by the number of scanning lines or pulses over the selected area at a given set of laser parameters. Alternatively, the surgeon may observe the color change of the ablated sclera tissue to determine when the ablation depth reaches the interface of the sclera and the ciliary.

The ablation patterns can be any symmetric shapes around the limbus area, including radial lines, arc or curved line, dotted rings. These are examples only but it can be more or less without departing from the spirit and scope of the invention. Enhancement may be performed by adding more ablation lines.

We are able to calibrate the ablation rate of various lasers on the sclera tissue by comparing the clinical data. To avoid the post-operative regression, the sclera tissue is permanently removed by the ablative lasers and filled in by the sub-conjunctival tissues.

The concept presented in the present patent is to remove, by any methods laser or non-laser, portion of the sclera tissue which is filled in by sub-conjunctiva tissue to increase the flexibility of the scleral area and in turn causes the zonular fiber to increase the lens accommodation. Therefore the laser ablation effects on the scleral tissue may also be conducted by any non-laser methods such as using a diamond knife which removes the scleral tissue at a width about (0.5–2.0) mm and length of (2.0–4.0) mm, as far as this area can be filled in by the sub-conjunctival tissue.

Another important concept proposed in the present invention is to support the post-operative results which show minimum regression. We proposed that the laser ablated sclera tissue "gap" will be filled in by the sub-conjunctival tissue within few days after the surgery. This filled in sub-conjunctival tissue is much more flexible than the original sclera tissue. Therefore the filled-in gap in the sclera area will cause the underlaying ciliary body to contract or expand the zonular fiber connected to the lens when the presbyopic patient is adjusting his lens curvature to see near and far.

The invention having now been fully described, it should be understood that it may be embodied in other specific forms or variations without departing from the spirit or essential characteristics of the present invention. Accordingly, the embodiments described herein are to be considered to be illustrative and not restrictive.

I claim:

1. A laser beam ophthalmic surgery method for treating presbyopic patient by removing a portion of the scleral tissue of an eye in a predetermined pattern and area, whereby the accommodation of the presbyopic eye increases via the movement of the ciliary body and zonular fiber connected to the lens of the eye, the predetermined pattern having a depth of about (60%–90%) of a scleral tissue thickness.

2. A laser beam ophthalmic surgery method for treating presbyopic patient by removing a portion of the scleral tissue of an eye in accordance with claim 1 in which said movement of the ciliary body is provided by the increase of the flexibility of said scleral tissue provided by the sub-conjunctival tissue filling of the laser-removed area of said scleral tissue.

3. A laser beam ophthalmic surgery method for treating presbyopic patient by removing a portion of the scleral tissue of an eye in accordance with claim 1 in which said scleral tissue removed by said laser beam is permanent, whereby the regression effects of the surgery is minimum.

4. A laser beam ophthalmic surgery method for treating presbyopic patient by removing portion of the scleral tissue of an eye in accordance with claim 1 in which said predetermined pattern includes at least 3 radial lines around the area of the cornea outside the limbus and each radial line has a dimension of about (0.1–1.0) mm in width and (2.0–5.0) mm in length.

5. A laser beam ophthalmic surgery method for treating presbyopic patient by removing portion of the scleral tissue of an eye in accordance with claim 1 in which said predetermined pattern includes at least 3 curved lines around the area of the cornea outside the limbus.

6. A laser beam ophthalmic surgery method for treating presbyopic patient by removing portion of the scleral tissue of an eye in accordance with claim 1 in which said predetermined pattern includes a dotted ring pattern around the area of the cornea outside the limbus and each dot has a size of about (0.1–1.0) mm in diameter.

7. A laser beam ophthalmic surgery method for treating presbyopic patent by removing portion of the scleral tissue of an eye in accordance with claim 1 in which said predetermined area is outside the limbus of the cornea defined by two circles having a diameter of about 10 mm and 18 mm.

8. A laser beam ophthalmic surgery method for treating presbyopic patient by removing portion of the scleral tissue of an eye in accordance with claim 1 in which said laser beam is a ultraviolet laser having a predetermined wavelength of about (0.15–0.36) microns.

9. A laser beam ophthalmic surgery method for treating presbyopic patient by removing portion of the scleral tissue of an eye in accordance with claim 1 in which said laser beam is an infrared laser having a predetermined wavelength of about (0.9–10.6) microns.

10. A laser beam ophthalmic surgery method for treating presbyopic patient by removing portion of the scleral tissue of an eye in accordance with claim 1 in which said laser beam is a short pulse solid state laser having a predetermined wavelength of about (0.5–1.4) microns and a pulse width of about one femtosecond to one nanoseconds.

11. The method of claim 8 wherein said laser beam includes is a solid state YAG-based laser frequency shifted to about (190–220) nm.

12. The method of claim 8 where said laser beam includes excimer lasers at wavelength of (193–310) nm.

13. The method of claim 9 wherein said laser beam is a solid state Er:YAG laser at 2.94 microns.

14. The method of claim 9 wherein said laser beam is an infrared gas laser.

15. A laser beam ophthalmic surgery method for treating presbyopic patient by removing portion of the scleral tissue of an eye in accordance with claim 1 in which said predetermined pattern is generated by a scanning device.

16. The method of claim 15 wherein said scanning device comprises of a motorized mirror device.

17. The method of claim 15 wherein said scanning device comprises of a refractive optics device.

18. A laser beam ophthalmic surgery method for treating presbyopic patient by removing portion of the scleral tissue of an eye in accordance with claim 1 in which said laser beam is delivered to said predetermined area by an articulate arm.

19. A laser beam ophthalmic surgery method for treating presbyopic patient by removing portion of the scleral tissue of an eye in accordance with claim 18 in which said predetermined pattern is generated by movement of said articulate arm.

20. A laser beam ophthalmic surgery method for treating presbyopic patient by removing portion of the scleral tissue of an eye in accordance with claim 1 in which said laser beam is delivered to said predetermined area by an optical fiber.

21. The method of claim 20 wherein said optical fiber is connected to a fiber hand piece having a fiber tip.

22. A laser beam ophthalmic surgery method for treating presbyopic patient by removing portion of the scleral tissue of an eye in accordance with claim 21 in which said predetermined pattern is generated by movement of said fiber tip on said predetermined area.

23. The method of claim 21 wherein said fiber tip produces a circular spot laser beam having a diameter about (0.1–1.0) mm.

24. The method of claim 21 wherein said fiber tip produces a line-shape laser beam having a dimension of about (0.1–1.0) mm in width and about (2.0–5.0) mm in length.

25. A laser beam ophthalmic surgery method for treating presbyopic patient by removing portion of the scleral tissue of an eye in accordance with claim 1 in which said predetermined pattern has a depth of about (300–600) microns controlled by number of laser pulses delivered to the sclera.

26. An ophthalmic surgery method for treating presbyopic patient by removing a portion of the scleral tissue of an eye in a predetermined pattern and area, whereby the accommodation of the presbyopic eye increases via the movement of the zonules connected to the lens, the predetermined pattern having a depth of about (60%–90%) of a scleral tissue thickness.

27. An ophthalmic surgery method for treating presbyopic patient by removing a portion of the scleral tissue of an eye in accordance with claim 26 in which the said scleral tissue is removed by a mechanical device.

28. The method of claim 27 wherein said mechanical device includes a surgical knife.

29. An ophthalmic surgery method for treating presbyopic patient by removing a portion of the scleral tissue of an eye in accordance with claim 26 in which said movement of the zonules is caused by the increase of the flexibility of said scleral tissue provided by the sub-conjunctival tissue filing of said mechanical device removed area of said scleral tissue.

30. An ophthalmic surgery method for treating presbyopic patient by removing a portion of the scleral tissue of an eye in accordance with claim 26 in which said predetermined pattern has a depth of about (300–600) microns.

* * * * *